United States Patent [19]

Stapp

[11] 4,152,295

[45] May 1, 1979

[54] CATALYST FOR THE OXIDATION OF A CONJUGATED DIOLEFIN

[75] Inventor: Paul R. Stapp, Bartlesville, Okla.

[73] Assignee: Phillips Petroleum Company, Bartlesville, Okla.

[21] Appl. No.: 883,013

[22] Filed: Mar. 3, 1978

Related U.S. Application Data

[62] Division of Ser. No. 713,777, Aug. 12, 1976, Pat. No. 4,093,815.

[51] Int. Cl.$^2$ .................... B01J 31/02; B01J 31/04
[52] U.S. Cl. .................... 252/430; 252/428; 252/429 R; 252/431 C; 560/246
[58] Field of Search .................. 252/428, 429 R, 430, 252/438, 440, 441, 462, 431 C; 560/246

[56] References Cited

U.S. PATENT DOCUMENTS

| 3,308,197 | 3/1967 | Bajars | 252/462 |
| 3,637,515 | 1/1972 | Huguet | 560/246 |

Primary Examiner—Winston A. Douglas
Assistant Examiner—P. E. Konopka

[57] ABSTRACT

A conjugated diolefin is reacted with at least one compound selected from the group consisting of a carboxylic acid and a carboxylic acid anhydride in the presence of oxygen and a catalyst comprising a rare earth metal compound, an alkali metal compound and a halide compound.

8 Claims, No Drawings

CATALYST FOR THE OXIDATION OF A CONJUGATED DIOLEFIN

This application is a division of my copending application Ser. No. 713,777 filed Aug. 12, 1976, now U.S. Pat. No. 4,093,815 issued June 6, 1978.

BACKGROUND OF THE INVENTION

The invention relates to a method suitable for the oxidation of a conjugated diolefin. In another aspect the invention relates to a composition useful as a catalyst.

It is desirable to oxidize conjugated diolefins, such as 1,3-butadiene and/or 2-methyl-1,3-butadiene to produce various compounds such as the ethylenically unsaturated esters of such diolefins. A more specific illustration is the oxidation of 1,3-butadiene to produce 1,4-diacetoxy-2-butene. The diacetoxybutene is then easily converted, by processes well known in the art, to other compounds such as tetrahydrofuran or 1,4-butanediol. Although there are various processes and catalysts known which are useful for the oxidation of a conjugated diolefin, most of these processes are relatively expensive to carry out and frequently corrosion of process equipment is a problem. Therefore new processes and catalysts are desirable in an effort to more fully develop the art and improve the overall process.

An object of the present invention is to oxidize a conjugated diolefin.

Another object of the invention is to oxidize a conjugated diolefin more economically than can be done presently.

Another object of the invention is to provide a catalyst useful for the oxidation of conjugated diolefins.

Other objects, advantages and aspects of the present invention will be apparent to those skilled in the art after studying the specification and appended claims.

SUMMARY OF THE INVENTION

In accordance with the invention a conjugated diolefin is reacted with a compound selected from the group consisting of a carboxylic acid and a carboxylic acid anhydride in the presence of oxygen and a catalyst comprising a rare earth metal compound, an alkali metal compound and a halide compound.

Further in accordance with the invention a composition useful as a catalyst comprises a rear earth metal compound, an alkali metal compound and a halide compound.

DETAILED DESCRIPTION OF THE INVENTION

The conjugated diolefins suitable for use in the process of the invention are selected from a wide range of compounds. Generally the conjugated diolefins employed in the process of the instant invention are those having from 4 to 12 carbon atoms per molecule. Suitable conjugated diolefins include acyclic as well as cyclic compounds and further include compounds which have substituents such as a halogen, cyano, or carbalkoxy radical present in the molecule. Presently preferred conjugated diolefins are those containing only carbon and hydrogen because use of such materials produces products finding particular applicability today. For the same reason, the compounds especially preferred for use in the instant invention are 1,3-butadiene and 2-methyl-1,3-butadiene (isoprene) to produce the corresponding diacetoxy derivatives. Examples of suitable conjugated diolefins besides 1,3-butadiene and 2-methyl-1,3-butadiene include 2-chloro-1,3-butadiene; 2-ethyl-1,3-butadiene, 2-chloro-3-methyl-1,3-butadiene; 1,3-hexadiene; 1,3-pentadiene; 1,3-octadiene; 1,3-cyclohexadiene; 1,3-cyclooctadiene; 1,3-cyclododecadiene; 2-cyano-1,3-butadiene; and 2-carbethoxy-1,3-butadiene. Mixtures of conjugated olefins are also suitable; however, a mixture of products will result which may be difficult to separate into the individual component products.

The conjugated diolefin is reacted with at least one compound selected from the group consisting of a carboxylic acid and a carboxylic acid anhydride to produce the corresponding diacyloxyalkene. In most instances it is preferred to use a carboxylic acid and the corresponding acid anhydride because the use of the corresponding acid anhydride, in addition to the carboxylic acid, serves to simplify the purification and separation steps by reducing the amount of by-products which contain free hydroxy groups. However, it is within the scope of the invention to use a carboxylic acid alone, a carboxylic acid anhydride alone, a carboxylic acid or a carboxylic acid and the corresponding acid anhydride. If the reaction is carried out using a carboxylic acid and a carboxylic acid anhydride of a different carboxylic acid, a mixture of reaction products normally results.

The carboxylic acids and acid anhydrides suitable for use in the invention are selected from a large variety of compounds. Generally the acids and acid anhydrides include mono- and dicarboxylic acids and acid anhydrides having from about 2 to about 18 carbon atoms per molecule. Such compounds include both aromatic and aliphatic compounds. Furthermore, they can contain halogen or cyano groups or other substituents which are essentially inert to the oxidizing conditions employed for the process of this invention. It is preferred, of course, that the carboxylic compounds employed be normally liquid or at least liquid under the reaction conditions for ease in handling. Acetic acid and acetic anhydride are presently the preferred carboxylic acid and acid anhydride for use according to the process of this invention. Examples of other suitable carboxylic acids include propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, and the respective acid anhydrides. Mixtures of carboxylic acids and acid anhydrides are also suitable; however, a mixture of reaction products normally results.

The catalyst system employed for the oxidation of the conjugated diolefins in accordance with the invention comprises three components. The first component of the instant catalyst system is a compound of an element having an atomic number within the range of 57 through 71, i.e., a compound of a rare earth metal. A suitable rare earth metal compound includes an oxide, carboxylate, nitrate, sulfate, halide and the like. Mixtures of said rare earth compounds can also be employed if desired. For example, it is well known that there are commercially available mixtures of rare earth compounds which have been termed in the art, didymium salts, and the term didymium itself has been applied to certain mixtures of the rare earth elements derived from the mineral monazite. Specifically, according to the fifth edition of the Condensed Chemical Dictionary, published by Reinhold Publishing Company, the term didymium is defined as the name applied to commercial mixtures of rare earth elements obtained from monazite sand by extraction followed by the elimination of cerium from the mixture. The name is used like that of an element in naming mixed oxides and salts. The approximate composition of didymium from monazite, expressed as rare earth oxides, is 45.5 per cent lanthana, 11 per cent praseodymia, 38 per cent neodymia, 4 per cent samaria, 0.4 per cent yttrium earth oxides and 1.1 per cent others. Examples of suitable rare earth compounds include the following: $CeO_2$, $CeCl_3$, $CeBr_3$, Ce(III) acetate, $PrBr_3$, $PrO_2$, $PrCl_3$, Pr(III) acetate, Nd(III) acetate, $NdBr_3$, $Nd_2O_3$, $NdCl_3$, Sm(III) acetate, Ce(III) nitrate, Ce(III) sulfate, $SmBr_3$, $SmCl_2$, $Sm_2O_3$, $EuBr_3$, $EuCl_3$, $Eu_2O_3$, $Gd_2O_3$, $GdCl_3$, $TbBr_3$, $Tb_2O_3$, Dy(III) acetate, $Dy_2O_3$, $DyCl_3$, $Dy_3(CO_3)_3$, $Er_2O_3$, $ErBr_3$, Er(III) acetate, $HoBr_3$, $HoCl_3$, $Ho_2O_3$, $TmBr_3$, $Tm_2O_3$, $YbBr_3$, $YbCl_2$, Yb(III) oxalate, $Yb_2O_3$, $LuBr_3$, $LuCl_3$, $Lu_2O_3$, and mixtures thereof and didymium salts such as didymium acetate, didymium carbonate, didymium oxide, and didymium chloride and mixtures of such didymium salts.

The second component of the instant catalyst system is an alkali metal compound. Suitable alkali metal compounds can be selected from a wide variety of such compounds, as for example, halides, carboxylates, oxides and the like. Of the alkali metal compounds which can be employed, the lithium compounds are especially preferred for use as the alkali metal compounds for the catalyst of this invention because they are generally more soluble in the reaction mixture. The amount of alkali metal compound employed is such that the molar ratio of rare earth metal compound to alkali metal compound is in the range of from about 0.05/1 to about 2/1 although good results were obtained employing a molar ratio of from about 0.1/1 to about 0.5/1. Examples of suitable alkali metal compounds include lithium chloride, lithium bromide, lithium iodide, lithium acetate, lithium benzoate, lithium oxide, lithium octadecanoate, sodium chloride, sodium bromide, sodium acetate, potassium chloride, potassium acetate, potassium benzoate, rubidium chloride, rubidium bromide, rubidium acetate, cesium chloride, cesium acetate, cesium oxide, and mixtures thereof.

The third component of the catalyst system of this invention is a source of halide, generally bromine, chlorine or iodine, with bromine and chlorine the most common. Said source of halides includes ionic halide or organohalide compounds. The necessary halide for the third component of the instant catalyst system can be provided by utilization of a halide compound which also has the first and/or second component of the catalyst system. The amount of the halide component required according to this invention is expressed as a ratio of the moles of the first component to equivalents of halide expressed as halide ion. Generally this ratio will be in the range of from 1/1 to 1/20, preferably from 1/3 to 1/10. It is also preferred if an organohalide is utilized as the third component, that said compounds be selected from the dihalo butenes such as 1,4-dibromo-2-butene, 1,4-dichloro-2-butene, 1,4-diiodo-2-butene or other isomers of these compounds.

The catalyst concentration employed for the instant invention is expressed in terms of mole percent rare earth metal based on the conjugated diolefin employed. The catalyst is effective over a broad range of catalyst concentrations. Generally, the amount of catalyst employed is in the range of from about 0.1 to about 20 mole percent rare earth metal compound although good results were obtained using from about 1 to about 15 mole percent of the rare earth metal compound based on the conjugated diolefin charged.

The reaction of the instant invention is an oxidation reaction and as such is carried out in the presence of free oxygen. The amount of oxygen present is not believed to be critical although it is recognized that an undesirably slow reaction will result if the concentration of oxygen is very low. Essentially pure oxygen can be employed as well as mixtures of oxygen with inert gases, or air can be employed as a source of free oxygen for the instant reaction. It is recognized that explosive conditions could be obtained if the amount of oxygen added to the reaction system is not under control. The reaction of this invention, as is true with many oxidation reactions, appears to be highly exothermic and this too dictates caution in adding oxygen to the system. Because of these considerations, it is desirable to add the oxygen incrementally or continuously during the reaction to avoid the explosive range of oxygen concentration and to allow better control of the temperature of the reaction. A reaction vessel with efficient mixing means is also desirable to avoid buildup of dangerous concentrations of free oxygen.

The temperature at which the reaction of this invention is carried out is selected over a relatively wide temperature range. Generally a temperature range of from about 30° to about 200° C. is employed; however, temperatures ranging from about 100° to about 150° C. were used with good success.

Similarly, the oxygen pressure at which the reaction is carried out can be selected over a relatively wide range. Generally the oxygen pressure ranges from about 0.1 to about 1000 psig of oxygen above autogenous pressure of the reactants in the absence of oxygen at the temperature employed; however, good results were obtained employing a range from about 5 to about 200 psig of oxygen above autogenous pressure at the temperature employed.

The reaction time generally depends on the temperature, catalyst activity, the reactants, and the oxygen pressure employed. The reaction time is usually based on the desired conversion of the starting diolefin reactant. The reaction time does not appear to be a particularly significant parameter of the reaction and in some cases a product can probably be produced at very low yields using a reaction time as short as a second; however, much longer reaction times are normally used ranging from about 1 to about 24 hours. Good results were obtained employing a reaction time ranging from about 5 to about 6 hours.

As described above, the reaction of the instant invention is carried out in the presence of a carboxylic acid and/or acid anhydride which provides the acyl moiety of the final product. In most instances, as previously described, it is desirable to employ as part of the reacton mixture the corresponding carboxylic anhydride (in addition to the carboxylic acid) as an optional but preferred component because the carboxylic acid anhydride serves to simplify the purification and separation steps by reducing the amount of by-products which contain free hydroxy groups. When both a carboxylic acid and the corresponding acid anhydride are used, it is desirable to use at least an amount of the acid anhydride equal to the amount of conjugated diolefin on a molar basis because for each mole of the diacyloxyalkene produced, one mole of water is also produced.

The process of the instant invention can be carried out in a batch or a continuous fashion.

Reaction mixtures obtained according to the process of this invention are generally vented to remove any unreacted oxygen and conjugated diolefin and then distilled to remove the carboxylic acid present. The product remaining is usually distilled to recover one or more fractions containing the diacyloxy olefins. The catalyst is usually recovered from the distillation residue and recycled to the reaction zone.

The isomeric materials which are recovered from the product mixture include in many instances an amount of 1,2-isomer which can be recycled to the reaction zone and thereby converted to the more desirable 1,4-diacyloxy olefin.

The above-mentioned 1,4-diacyloxy olefins have utility as intermediates for the preparation of the corresponding saturated diols. For example, as previously noted, it is known to prepare tetrahydrofuran or 1,4-butanediol starting with a conjugated diolefin and proceeding through 1,4-diacyloxy butene.

EXAMPLE I

A run was carried out according to the instant invention employing a 250 ml Fisher-Porter aerosol compatibility bottle equipped with a magnetic stirrer as the reaction vessel. The reactor was charged with 3.4 grams (20 millimoles) of ceric oxide ($CeO_2$), 6.5 grams (75 millimoles) of lithium bromide, 4.6 grams (21.5 millimoles) of 1,4-dibromo-2-butene, 50 ml of acetic acid, 25 ml of acetic anhydride and 10.3 grams (190.7 millimoles) of butadiene charged from the vapor phase. The reactor was pressured to 30 psig with oxygen, placed in an oil bath and heated to 140° C. About one hour was required to bring the temperature of the bath up to the desired reaction temperature and a reaction time of 5 hours was employed. During the course of the 5-hour reaction period, the reactor was charged with additional oxygen intermittently by pressuring the reactor to about 120 psig with oxygen. At the end of the reaction period, the reactor was vented and the reaction mixture filtered to recover 9.0 grams of a black solid residue. The filtrate was transferred to a distilling flask and the acetic acid was distilled away at 50 millimeters mercury pressure. The distillation residue was mixed with diethyl ether and water and filtered through celite. The aqueous layer was extracted with ether. The combined ether extracts were washed with water, washed with sodium carbonate solution, and then dried over magnesium sulfate and filtered. The ether was removed on a rotary evaporator to leave 19.7 grams of a dark oil. This material was analyzed by gas-liquid chromatography (GLC) which revealed that 3.77 grams (21.9 millimoles) of 1,2-diacetoxy-3-butene and 15.44 grams (89.8 millimoles) of 1,4-diacetoxy-2-butene had been obtained in this reaction. The yield of diacetoxy butenes based on the butadiene charged was 59 per cent.

If it is assumed that all of the 1,4-di-bromo-2-butene was converted to diacetoxy butenes, then the yield of diacetoxy butenes based on the butadiene charged was 47.3 per cent.

This example provides a demonstration of operability of the instant invention, i.e., the oxidation of butadiene in acetic acid media to produce diacetoxy butenes with $CeO_2$/LiBr/1,4-di-bromo-2-butene as the catalyst.

EXAMPLE II

Another run was conducted employing the same apparatus as that used in Example I but in this run there was no source of halide in the catalyst system. The reactor was charged with 3.4 grams (20 millimoles) of ceric oxide, 7.6 grams (75 millimoles) of lithium acetate dihydrate, 50 ml of acetic acid, 25 ml of acetic anhydride, and 10.0 grams (185.2 millimoles) of butadiene charged from the vapor phase. The reactor was placed in an oil bath, pressured to 30 psig with oxygen and heated to 140° C. About one hour was required for the oil bath temperature to reach the reaction temperature desired, after which a reaction period of 5.3 hours was employed. During the reaction the reactor was pressured to 120 psig with oxygen intermittently. At the end of the reaction period (5.3 hours) the reactor was vented and 1.8 grams of unreacted butadiene was recovered in a cold trap. The reaction mixture was diluted with ether and 2.67 grams of a solid pecipitate was collected by filtration and dried. The ether solution filtrate was washed with water, neutralized with sodium carbonate solution, dried over magnesium sulfate, filtered, and the ether then removed by distillation. The distillation residue (21.3 g) was a pale brown oil. It was analyzed by gas-liquid chromatography which showed that the residue was 86 per cent. ether with the remainder being the diacetoxy butenes. Specifically, there was produced 11 millimoles of 1,2-diacetoxy-3-butene and 3 millimoles of 1,4-diacetoxy-2-butene for a total yield of 14 millimoles of diacetoxy butenes which represents a yield of 7 per cent bases on the butadiene charged.

Comparison of the results of this run with Example I demonstrate that much inferior results are obtained if a source of chlorine or bromine is not provided for the catalyst system in the oxidation of butadiene to diacetoxy butenes with a combination of rare earth compounds and alkali metal compounds as the catalyst.

EXAMPLE III

Another run was carried out similar to that of Example I but without the presence of the alkali metal component. A 250 ml Fisher-Porter aerosol compatibility bottle equipped with magnetic stirring means was charged with 3.4 grams (20 millimoles) of ceric oxide, 12.6 grams (59 millimoles) of 1,4-dibromo-2-butene, 50 ml of acetic acid, 25 ml of acetic anhydride, and 11.3 grams (209.2 millimoles) of butadiene charged in the vapor phase. The bottle was placed in an oil bath, pressured to 30 psig with oxygen and heated to 140° C. About 40 minutes was required for the temperature of the bath to reach the desired reaction temperature. The reaction was continued for a period of 5 hours during which time the oxygen pressure was maintained at about 100 psig by intermittent pressuring of the reaction vessel with oxygen. At the end of the reaction period, the bottle was vented. The weight of the entire reaction mixture indicated a weight gain during the oxidation reaction of 5.7 grams. The whole reaction mixture was transferred, utilizing acetic acid as the rinsing medium, to a distilling flask and the acetic acid then removed by distillation through an 18 inch Vigreaux column at 50 mm mercury pressure. The overhead material recovered during this distillation weighed 95.7 grams. The distillation residue which was a nearly solid, black carbonaceous material weighing 38.4 grams was contacted with a mixture of ether and water. The layers were separated and the aqueous layer extracted with ether followed by filtration of the combined ether extracts. The ether solution was washed with an aqueous sodium carbonate solution, dried over anhydrous magnesium sulfate and then filtered prior to removal of the ether on a rotary evaporator. There was recovered 18.0 grams of a dark oil after the ether was evaporated. This material was analyzed by gas-liquid phase chromatography which demonstrated that there was present 3.29 grams (19.1 millimoles) of 1,2-diacetoxy-3-butene, 1.31 grams (7.6 millimoles) of cis-1,4-diacetoxy-2-butene and 5.87 grams (34.1 millimoles) of trans-1,4-diacetoxy-2-butene for a combined yield of 29.1% of diacetoxybutenes based on the butadiene charged.

It is noted that the amount of bromide ion (or equivalent) was the same in this run as that utilized in Example I and the amount of ceric oxide and other reaction materials including acetic acid and acetic anhydride were also the same as in Example I. However, there was no alkali metal component utilized in the catalyst system. It can be seen that the yield of diacetoxybutenes obtained in Example I, which was 59%, is twice that obtained in this example carried out without the presence of the alkali metal component. Or if it is assumed that all of the 1,4-dibromo-2-butene was converted to diacetoxy butenes, then the yield of diacetoxy butenes based on the butadiene charged was only 0.9 per cent in this example as compared to a yield of 47.3% in Example I. These results clearly show that the yields are drastically reduced if the alkali metal component is not employed and thus the necessity for employing such component.

What is claimed is:

1. A composition consisting essentially of a rare earth metal compound, an alkali metal compound and a halide compound
    wherein the rare earth metal compound is selected from the group consisting of rare earth metal oxides, carboxylates, nitrates, halides, sulfates and mixtures thereof,
    wherein the alkali metal compound is selected from the group consisting of alkali metal halides, carboxylates, oxides, and mixtures thereof
    and wherein the halide compound is selected from the group consisting of 1,4-dibromo-2-butene, 1,4-dichloro-2-butene, 1,4-diiodo-2-butene and mixtures thereof,
    and wherein the ratio of the mols of rare earth metal compound to the mols of alkali metal compound is within the range of about 0.05:1 to about 2:1.

2. A composition according to claim 1 wherein the rare earth metal compound is selected from the group consisting of $CeO_2$, $CeCl_3$, $CeBr_3$, Ce(III) acetate, $PrBr_3$, $PrO_2$, $PrCl_3$, Pr(III) acetate, Nd(III) acetate, $NdBr_3$, $Nd_2O_3$, $NdCl_3$, Sm(III) acetate, Ce(III) nitrate, Ce(III) sulfate, $SmBr_3$, $SmCl_2$, $Sm_2O_3$, $EuBr_3$, $EuCl_3$, $Eu_2O_3$, $Gd_2O_3$, $GdCl_3$, $TbBr_3$, $Tb_2O_3$, Dy(III) acetate, $Dy_2O_3$, $DyCl_3$, $Dy_2(CO_3)_3$, $Er_2O_3$, $ErBr_3$, Er(III) acetate, $HoBr_3$, $HoCl_3$, $Ho_2O_3$, $TmBr_3$, $Tm_2O_3$, $YbBr_3$, $YbCl_2$, Yb(III) oxalate, $Yb_2O_3$, $LuBr_3$, $LuCl_3$, $Lu_2O_3$, and didymium salts such as didymium acetate, didymium carbonate, didymium oxide, and didymium chloride.

3. A composition according to claim 1 wherein the halide compound provides a source of bromine, chlorine or mixtures thereof.

4. A composition according to claim 1 wherein the ratio of the moles of rare earth metal compound to the moles of the alkali metal compound is within a range of about 0.1:1 to 0.5:1.

5. A composition according to claim 1 wherein the ratio of the moles of the rare earth metal compound to the equivalents of halide expressed as halide ion is within a range of about 1:1 to about 1:20.

6. A composition according to claim 4 wherein the ratio of the moles of the rare earth metal compound to the equivalents of halide expressed as halide ion is within a range of about 1:3 to about 1:10.

7. A composition according to claim 1 wherein the alkali metal is lithium.

8. A composition according to claim 1 wherein the alkali metal compound is selected from the group consisting of lithium chloride, lithium bromide, lithium iodide, lithium acetate, lithium benzoate, lithium oxide, lithium octadecanoate, sodium chloride, sodium bromide, sodium acetate, potassium chloride, potassium acetate, potassium benzoate, rubidium chloride, rubidium bromode, rubidium acetate, cesium chloride, cesium acetate, cesium oxide, and mixtures thereof.

* * * * *